United States Patent [19]

Rowan et al.

[11] Patent Number: 5,106,621
[45] Date of Patent: Apr. 21, 1992

[54] CYSTEINE PROTEINASES, PRODUCTION AND USE

[76] Inventors: Andrew D. Rowan, 69 Roseford Road, Cambridge, CB4 2HA; David J. Buttle, 5 Hobart Road, Cambridge, CB1 3PU, both of England

[21] Appl. No.: 622,215

[22] Filed: Nov. 30, 1990

Related U.S. Application Data

[63] Continuation of Ser. No. 259,133, Oct. 18, 1988, abandoned.

[30] Foreign Application Priority Data

Oct. 22, 1987 [GB] United Kingdom ............... 8724728

[51] Int. Cl.$^5$ .............................................. A61K 37/54
[52] U.S. Cl. ............................. 424/94.65; 424/195.1; 424/DIG. 13; 435/219
[58] Field of Search .................. 424/94.65, 195.1; 435/219

[56] References Cited

U.S. PATENT DOCUMENTS

| | | | |
|---|---|---|---|
| 2,950,227 | 8/1960 | Gibian et al. | 195/66 |
| 3,002,891 | 10/1961 | Heinicke | 195/66 |
| 4,197,291 | 4/1980 | Klein et al. | 424/94 |
| 4,226,854 | 10/1980 | Klein et al. | 424/94 |
| 4,286,064 | 8/1981 | Galbraith | 435/219 |
| 4,329,430 | 5/1982 | Klein et al. | 435/219 |
| 4,361,551 | 11/1982 | Galbraith | 424/94.2 |
| 4,645,668 | 2/1987 | Pinnell | 424/94 |

FOREIGN PATENT DOCUMENTS

WO81/01242  5/1981  PCT Int'l Appl. ............... 424/94.65

OTHER PUBLICATIONS

Klein, "Enzymatic Debridement of Third Degree Burns in Aminals with Bromelains—A Preliminary Report", J. of the Maine Medical Association, Sep. 1964.

Levenson et al., "Chemical Debridement of Burns", Annals of Surgery, 180: 670-704 (1974).

Levenson, "Burn Debridement", The J. of Trauma, 21:735-739 (1981).

Makepeace, "Enzymatic Debridement of Burns: A Review", Burns 9: 153-157 (1982).

Rowan et al., "Ananain: A Novel Cysteine Proteinase Found in Pineapple Stem," Archives of Biochem. and Biophys., 267: 262-270 (1988).

Obed et al., "Cysteine Proteinase Content of Rat Muscle Lysosomes: Evidence for an Unusual Proteinase Activity", BA 79(12):106026, 1984.

Levin et al., "Debridement of Experimental Skin Burns of Pigs with Bromelain, A Pineapple-Stem Enzyme", Plastic & Reconstructive Surgery, 52: 413-424 (1973).

Klaue et al., "Chemical Debridement of the Burn Eschar in Rats with Bromelain Combined with Topical Antimicrobial Agents," Eur. Surg. Res., 11: 353-359 (1979).

Houch et al., "Insolation of an Effective Debriding Agent from the Stems of Pineapple Plants," Int. J. Tiss. Reac. 2:125-134 (1983).

Analytical Biochemistry, vol. 62, 1974, pp. 478-484, Academic Press, Inc.

Silverstein, R. M., The Assay of the Bromelains Using N-CBZ-L-Lysine P-Nitrophenyl Ester and N-CB-Z-Glycine p-Nitrohenyl Ester as Substrates Analytical Biochemistry, vol. 62, pp. 478-484 (1974).

Biochemistry, vol. 3, No. 8, Aug. 1964, pp. 1050-1054, Feinstein et al., On the Molecular Weights of the Proteolytic Enzymes of Stem Bromelain.

J. Biochem., vol. 98, No. 1, 1985, pp. 219-228; S. Ota et al., Reinvestigation of Fractionation and Some Properties of the Proteolytically Active Components of Stem and Fruit Bromelains.

Biochem. J., vol. 221, 1984, pp. 445-452, GB; A. D. Gounaris et al., Human Plasma Alpha-Cysteine Proteinase Inhibitor.

Primary Examiner—Douglas W. Robinson
Assistant Examiner—Jean C. Witz

[57] ABSTRACT

A cysteine proteinase characterized in that it is immunologically distinct, has a molecular mass of about 25,000 and has a distinct net charge is disclosed. "Ananain" and "comosain" are such enzymes, which may be distinguished by their specificities for certain synthetic substrates.

A process for the production thereof is also disclosed which comprises separation from pineapple plant material and purification. Such enzymes may be used in the debridement of eschar tissues.

8 Claims, 7 Drawing Sheets

Fig. 7

CYSTEINE PROTEINASES, PRODUCTION AND USE

This is a continuation of copending application Ser. No. 07/259,133 filed on Oct. 18, 1988, now abandoned.

This invention relates to cysteine proteinases, to the production and use thereof; more particularly, it relates to two such enzymes, termed "ananain" and "comosain" herein, to the production thereof involving separation and purification in particular from pineapple stem extract, and to the use thereof in the debridement of eschar tissue of wounds.

Various cysteine proteinases are to be found in the latex and juice of several tropical plants; papain (EC 3.4.22.2) from *Carica papaya* latex being a well known example. Another cysteine proteinase is to be found in the leaves and stems of the pineapple plant (*Ananas comosus*) and is referred to as stem bromelain (EC 3.4.22.4).

Proteolytic enzymes have a wide variety of applications and one area which has attracted considerable attention is the use thereof in the early debridement (digestion and separation) of eschar tissues, such as in burn wounds, decubitus ulcers, pressure necroses and bed sores. The devitalised tissue in burns and sores for example, provides an excellent culture medium for opportunistic pathogens leading to a high frequency of septicemia and eventual death in the majority of severely burned patients. In an attempt to effect early debridement, various agents have been employed, such as pyruvic acid, tannic acid, salicylic acid, streptokinase, trypsin and papain. However, such attempts have been unsuccessful due to unacceptable toxicity or low activity.

The present invention provides a cysteine proteinase characterised in that it is immunologically distinct, has a molecular mass of about 25,000 and has a distinct net charge.

In one preferred embodiment, the present invention relates particularly to ananain, which may be isolated from pineapple plant material and which has substrate specificities and properties distinct from those of bromelain or other known proteinases. In another preferred embodiment, the present invention further relates to another cysteine proteinase, comosain, which is obtainable from such a source and which also has properties distinct from those of the two other proteinases mentioned as being present in pineapple stem.

The present invention also provides a process for the production thereof characterised in that it comprises separation from pineapple plant material, preferably powdered stem, and purification.

Such proteolytic enzymes may be used to enhance the process of debridement of eschar tissue resulting from various burn wounds, sores and ulcers, for example. An enzyme preparation may be specifically adapted for such utility. The present invention also relates thereto. More particularly, the present invention further provides a pharmaceutical composition which comprises at least one of the present cysteine proteinases and at least one pharmaceutically-acceptable carrier.

As indicated above, ananain is a biochemically distinct cysteine proteinase. It has a slightly lower relative molecular mass to bromelain, approx. 25,000 as opposed to 26,000 (see below), is a more basic protein, having a pI greater than 8.0, and a faster migration in a cathodal electrophoresis system (see below). The proteolytic activity of ananain against fibrin is twice that of bromelain and ananain has a different specificity for synthetic substrates (see below). Ananain is immunologically distinct from bromelain, as demonstrated by analysis on double immunodiffusion plates (see below). In keeping with its classification as a cysteine proteinase, ananain requires thiol compounds for full activity and is inhibited by the class-specific inhibitors E-64 [L-3-carboxy-2,3-trans-epoxypropionyl-leucylamido (4-guanidino) butane] and chicken cystatin (see below).

More particularly, ananain has an increased activity with hide powder azure and fibrin substrates and a lower activity with azocasein substrate than the major pineapple proteinase bromelain, for example. Ananain also hydrolyses the synthetic substrate α-N-benzyloxycarbonyl-L-phenylalanyl-L-arginyl 7-(4-methyl) coumarylamide (Z-Phe-Arg-NHMec), a substrate very pooly hydrolysed by stem bromelain. In view of its different substrate specificity and immunological reactivity, ananain is probably a unique gene product, distinct from bromelain.

As regards comosain, generally it shares the major physicochemical properties of ananain, its molecular weight and also its charge, however, its specificity differs for synthetic substrates (see below). In common with other cysteine proteinases, it requires thiol compounds for full activity and is inhibited by E64.

The present enzymes may be obtained by generally conventional preparative fast protein liquid chromatography (FPLC) cation-exchange chromatography at pH 5.0, for example, where they elute significantly later than the known bromelain fractions. Currently, commercially available crude pineapple extract powders are commonly used as a source of the present proteinases. However, freshly prepared pineapple stems or other parts of the plant may also be suitable. More specifically, an extract may be chromatographed using a cation exchanger (Mono S) using a Pharmacia FPLC system and a gradient of 0.05 to 1.0M sodium acetate, pH 5.0. A variety of substrates may be used to assay the fractions for cysteine proteinase activity and the different proteinases identified on the basis of the different substrate specificities thereof.

The present cysteine proteinases may be admixed with pharmaceutically-acceptable carriers for application to patients. The generally preferred route of administration is by topical application to the site of a burn wound or ulcer. The pharmaceutical preparation may be in the form of a sterile solution that is applied to an inert dressing, such as a gauze pad, or a gel or ointment that is placed directly on the wound. Several applications may be required to obtain complete debridement. A sterile solution, preferably an aqueous solution or suspension, may contain, in addition to the active ingredient(s), buffer salts or carriers, such as those described in general pharmaceutical tests, for example Remington's Pharmaceutical Sciences, Arthur Osol (Ed.), 16th Edition, Mack Publishing Co., Easton, Pa., USA, 1980. A gel or ointment formulation may additionally contain a pharmaceutically-acceptable thickening agent, such as polyethylene glycol, hyaluronic acid, carbapol or glycerol.

Such pharmaceutical compositions may contain the cysteine proteinase(s) in an active form, or, preferably, in an inactive form in which the active site cysteine residue forms half of a disulphide bridge. The other half thereof comprises a pharmaceutically-acceptable thiol compound, for example the amino acid cysteine. The present formulations may be prepared immediately before use by mixing a lyophilised preparation of the cysteine proteinase with an aqueous solution. If an enzyme is present in an inactive form, an activating agent, for example cysteine, must be added to regenerate the free active site thiol of the proteinase.

Cysteine proteinases and compositions in accordance with the present invention may be used in the debridement of eschar tissues.

Referring to the accompanying illustrative drawings.

The following illustrates the present invention.

EXAMPLE 1

Purification of Ananain From Crude Pineapple Stem Extract

Crude pineapple stem extract purchased from Sigma (Bromelain, Product No. B2252) was dissolved in 50 mM sodium acetate buffer, 1 mM EDTA, 0.01% sodium azide, pH 5.0. This was filtered through 0.22 μm filters and the protein content was determined by absorption at 280 nm using an $A_{1\%,280}$ of 20.1 (Murachi, T. and Yasui, M., Biochemistry, 4, 2275-2282, 1965). The preparation was then chromatographed on a Mono S HR 10/10 column of a FPLC system (Pharmacia) utilizing a gradient of 0.05 to 1.0M sodium acetate, pH 5.0, essentially as described previously for chymopapain (Buttle, D. J., and Barrett, A. J., Biochem. J., 223, 81-88, 1984) with a flow rate of 2.0 ml/min. Protein (80 mg) was applied to the column and 4 ml fractions were collected into tubes containing sufficient 100 mM hydroxyethyldisulphide to give a final concentration of 2 mM. Plots of $A_{280}$ and gradient composition were provided automatically. The fractions were stored, tightly capped at 4° C. until assayed and further processed. The two peaks eluting between 0.33 and 0.39M Na+, and 0.41 and 0.44M Na+ were taken and designated 'Peak 1 bromelain' and 'Peak 2 bromelain'. The peak enriched in ananain and comosain (Peak 3), eluting in the region 0.60 to 0.70M sodium ions (see accompanying FIG. 1), was concentrated and dialysed in an Amicon concentration/dialysis chamber against 50 mM sodium phosphate:ethylene glycol (2:1), 1 mM EDTA, 0.01% sodium azide, pH 6.8 at 4° C. This peak is also used for the subsequent purification of comosain (see Example 2). To an aliquot of this material containing approximately 10 mg of protein, dithiothreitol or cysteine was added to a final concentration of 2 mM or 4 mM, respectively, and left to activate for 20 minutes at 4° C. This was then applied to a 1 ml column of "Sepharose"-aminohexanoyl-Gly-Phe-Gly-Semicarbazide (Rich, D. H., et al, Biochem. J., 235, 731-734, 1986), followed by 10 ml of the above buffer. 50 mM sodium formate:ethylene glycol (2:1), 1 mM EDTA, 0.01% sodium azide, pH 4.0, containing a disulphide, either hydroxyethyldisulphide (50 mM), 2,2'-dipyridyl disulphide (1.5 mM) or a saturated filtered solution of cystine (1 ml) was then applied and the column was left in this buffer overnight at 20° C. before eluting with a further 2 ml of the same buffer. The column was then reequilibrated with 5 ml of the sodium phosphate buffer. The material eluted in disulphide was then applied to a Mono S HR 5/5 column equilibrated with 100 mM sodium chloride, 25 mM sodium tetraborate, 1 mM EDTA, 0.01% sodium azide, pH 9.0. The column was eluted with a linear gradient (10 mM Na+/ml) to 300 mM NaCl in the same buffer, at a flow rate of 0.5 ml/min. Fractions (0.2 ml) were collected into tubes containing hydroxyethyldisulphide to 2 mM. The major peak from this chromatographic run (eluting in the range 0.18-0.21M Na+) active against Z-Phe-Arg-NHMec, but showing little activity against Z-Arg-Arg-NHMec (see Example 4) was pooled and diluted with an equal volume of 25 mM sodium tetraborate, 1 mM EDTA, 0.01% sodium azide, pH 9.0 and reapplied to the same Mono S column and eluted as described above (see accompanying FIG. 2). The fractions active against Z-Phe-Arg-NHMec were then pooled and dialysed against 10 volumes of 1 mM EDTA for three changes, before being lyophilised.

EXAMPLE 2

Purification of Comosain

Figure 3:
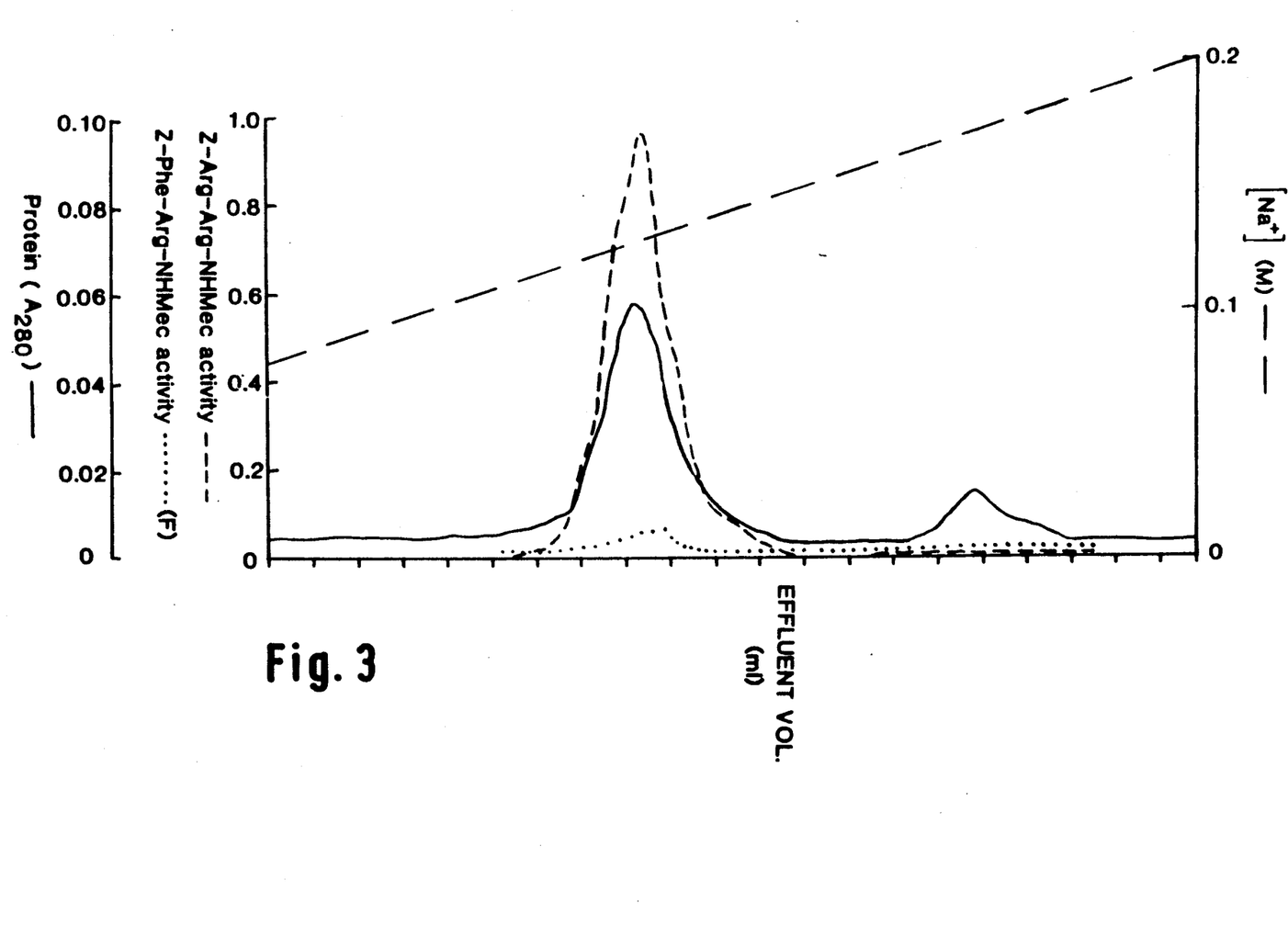
FIG. 3 depicts plots of $A_{280}$, substrate hydrolysis and gradient composition for comosain fractionated at pH 9.0 on FPLC Mono S HR 5/5.

Crude pineapple stem extract was chromatographed and the peak enriched in ananain and comosain eluting in the range 0.60-0.70M sodium acetate (FIG. 1) was concentrated and dialysed as described in Example 1. Affinity chromatography was then performed as described in Example 1, except that "Sepharose"-aminohexanoyl-Phe-Gly-semicarbazide (Rich, D. H.; loc cit) was used in place of the Gly-Phe-Gly-semicarbazide-containing gel. The material eluted in disulphide was then applied to a Mono S HR 5/5 column equilibrated with 100 mM sodium chloride, 25 mM sodium tetraborate, 1 mM EDTA, 0.01% sodium azide, pH 9.0. The column was eluted with a linear gradient (5 mM Na+/ml) to 300 mM sodium chloride in the same buffer at a flow rate of 0.5 ml/min. Fractions (0.2 ml) were collected into tubes containing hydroxyethyldisulphide to 2 mM. The peak eluting in the region 0.13-0.15M Na+ active against Z-Arg-Arg-NHMec was pooled and re-run on the same Mono S column and eluted as described in Example 1 (see accompanying FIG. 3). The fractions active against Z-Arg-Arg-NHMec were pooled, dialysed and lyophilized as in Example 1.

EXAMPLE 3

Assay of Protein Substrates (1) Azocasein assay:
  Proteolytic activity was assayed as described by Buttle and Barrett (loc cit).
(2) Hide powder azure assay:
  This assay was adapted from the method of Barrett, A. J., et al., Biochem J., 181, 401-408, 1979, for use with cysteine proteinases. The hide powder azure was purchased from Sigma. The test sample was added to 250 μl of 0.4M sodium phosphate, 4 mM EDTA, 8 mM dithiothreitol, pH 6.8, and allowed to activate for 5 min at 40° C., after which pre-warmed 0.01% Brij 35 was added to 700 μl, followed by 300 μl of substrate suspension, i.e. 33 mg of hide powder azure/ml in 0.6M sucrose. The tubes were incubated at 40° C. for 20 min in a rolling rack (2 rev/min.). The reaction was stopped by addition of 1.0 ml of 0.1M sodium mono-chloroacetate, 0.2M sodium acetate buffer, pH 4.3. After centrifugation (1200×g, 5 min), $A_{595}$ of the supernatant was determined. (See Table 1 below.)

(3) Fibrin assay:

This assay was adapted from the hide powder azure and azocasein protocols. The fibrin was purchased from Sigma. The test sample was added to 250 μl of the above pH 6.8 buffer and allowed to activate for 5 min at 40° C., after which pre-warmed 0.01% Brij 35 was added to 750 μl, followed by 250 μl of 6% fibrin (w/v) in water. The tubes were incubated for 60 min at 40° C. in a rotating rack (2 rev/min). The reaction was stopped by the addition of 5 ml of 0.1M sodium monochloroacetate, 0.2M sodium acetate buffer, pH 4.3. Undigested fibrin was filtered out and the amount of solubilised fibrin was measured at 280 nm. (See Table 1 below.)

(4) Azocoll Assay:

The azocoll was purchased from Sigma. The test sample was added to 125 μl of the above pH 6.8 buffer and allowed to activate for 5 min at 40° C., after which pre-warmed 0.01% Brij 35 was added to 400 μl, followed by 100 μl of 3% azocoll (w/v) suspension in 0.6M sucrose. The tubes were incubated at 40° C. for 20 min in a rolling rack (2 rev/min). The reaction was stopped by addition of 500 μl 20% (w/v) trichloroacetic acid. After centrifugation, the $A_{520}$ of the supernatant was determined.

TABLE 1

Relative enzyme activities of the three major peaks of the Sigma "Bromelain" against protein substrates

| | Relative Enzyme Activity (Arbitrary units normalized to azocasein) | | |
|---|---|---|---|
| Substrate | Peak 1 (Bromelain) | Peak 2 (Bromelain) | Peak 3 (Ananain and Comosain) |
| Azocasein | 1.000 | 1.000 | 1.000 |
| Azocoll | 2.078 | 2.014 | 1.708 |
| Blue Hide Powder | 0.765 | 1.000 | 4.401 |
| Fibrin | 0.465 | 0.455 | 2.473 |

Figure 1:
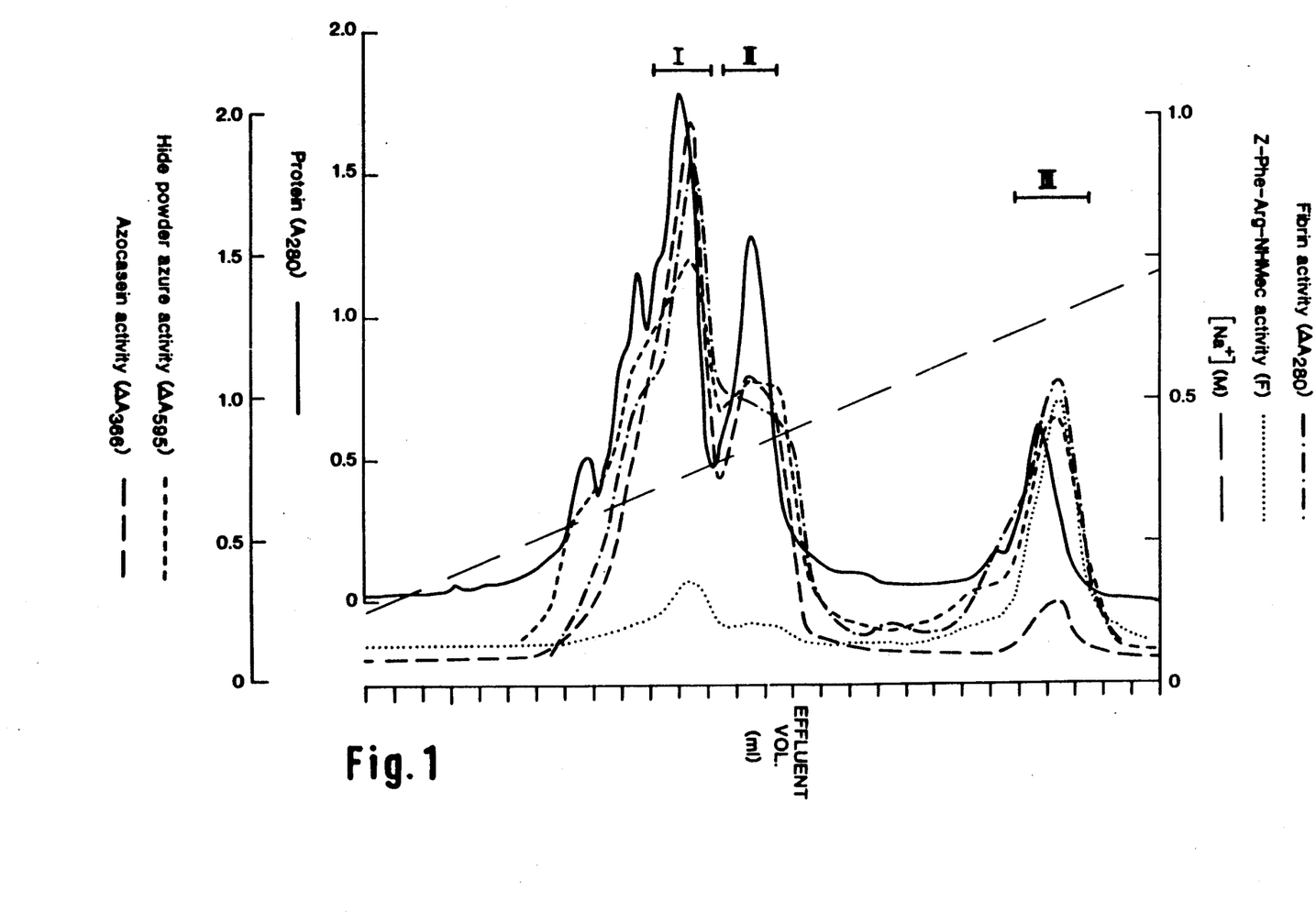
FIG. 1 depicts plots of $A_{280}$, substrate hydrolysis and gradient composition for crude stem bromelain fractionated on FPLC Mono S HR 10/10 at pH 5.0.
Figure 2:
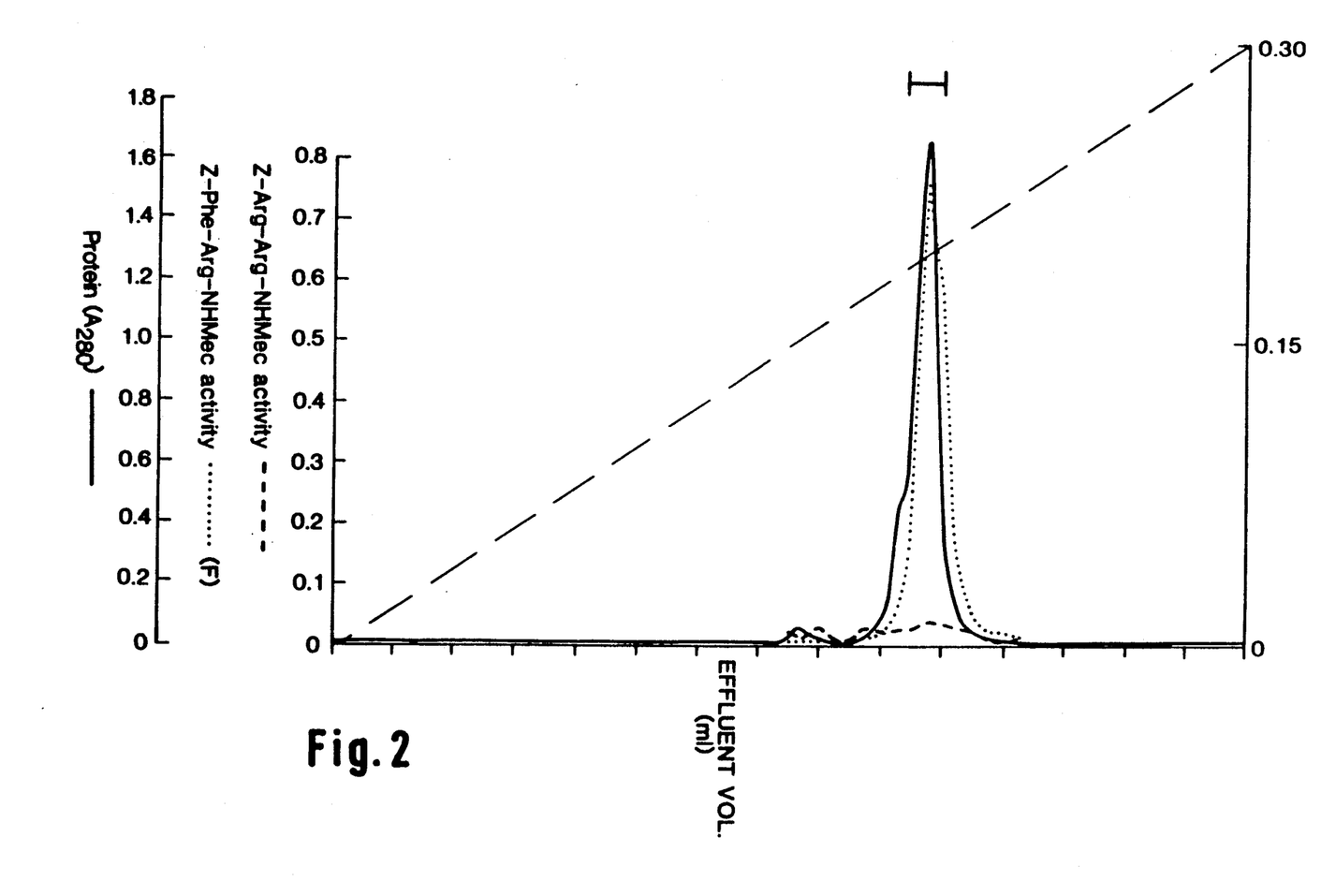
FIG. 2 depicts plots of $A_{280}$, substrate hydrolysis and gradient composition for ananain fractionated at pH 9.0 on FPLC Mono S HR 5/5.

"Peak 1" is the material eluting between 0.33 and 0.39 M Na+ in accompanying FIG. 1.
"Peak 2 " is the material eluting between 0.41 and 0.44 M Na+ in accompanying FIG. 1.
"Peak 3" is the material eluting between 0.60 and 0.70 M Na+ in accompanying FIG. 1, which is used for the purification of ananain and comosain.

EXAMPLE 4

Relative Activities of Purified Bromelain, Ananain and Comosain Against a Series of Aminomethylcoumarylamide-Containing Substrates The enzymes used were affinity purified ananain and comosain (Examples 1 and 2) and bromelain, which was obtained from chromatography-purified Sigma bromelain (catalogue number B 5144) by affinity chromatography on a column of Sepharose-aminohexanoyl-Gly-Phe-Gly-semicarbazide, followed by dialysis into 1 mM EDTA and lyophilisation. The proteinases were standardised by E-64 titration as described in Example 8.

Z-Phe-Cit-NHMec and Boc-Gly-NHMec were custom synthesized by Cambridge Research Biochemicals. Z-Gly-Phe-Cit-NHMec was a gift from Dr. C. J. Gray, Department of Biochemistry, Birmingham University, Birmingham, U.K. All other substrates were purchased from Bachem (Switzerland).

The enzyme sample was activated in 250 μl of the pH 6.8 activation buffer (Example 3) for 5 min, after which pre-warmed 0.01% Brij 35 was added, to 750 μl. The reaction was started by the addition of 250 μl of substrate (20 μM) in water. After a 10 min incubation at 40° C., the reaction was stopped with 1 ml of 0.10M sodium monochloroacetate, 0.20M sodium acetate buffer, pH 4.3. Fluorescence due to released 7-amino-4-methylcoumarin was measured in a fluorimeter (exitation 360 nm, emission 460 nm), standardised so that 1000 arbitrary units corresponded to 0.5 μM coumarin (i.e. at most, 10% substrate hydrolysis).

The results were expressed as nM coumarin released/min/nM active enzyme (see accompanying Table 2).

TABLE 2

Activities of ananain, bromelain and comosain against a variety of synthetic coumarylamide substrates.

| | nM coumarin released/min/nM active enzyme | | |
|---|---|---|---|
| Substrate | Ananain | Bromelain | Comosain |
| Z-Phe-Arg- | 12.1 | 2.2 | 8.7 |
| Z-Arg-Arg- | 0.3 | 216.7 | 263.3 |
| Z-Phe-Cit- | 24.0 | 0 | 19.3 |
| Z-Gly-Phe-Cit- | 153.0 | 0 | 63.3 |
| Bz-Phe-Val-Arg- | 216.0 | 3.9 | 118.0 |
| Z-Phe-Met- | 2.5 | 0.6 | 4.0 |
| Glt-Gly-Gly-Phe- | 0.1 | 1.1 | 0 |
| Boc-Gly- | 0 | 0.6 | 0 |
| Z-Gly-Gly-Arg- | 0.2 | 0 | 0 |
| Boc-Val-Pro-Arg- | 0.1 | 0 | 0 |
| Glt-Gly-Arg- | 0 | 0 | 0 |
| Suc-(Ala)$_2$-Pro-Phe- | 0 | 0 | 0 |

(Boc, t-butyloxycarbonyl; Bz, benzoyl; Cit, citrulline; Glt, glutaryl; Suc, succinyl.)

EXAMPLE 5

Kinetics of Hydrolysis of Two Fluorimetric Substrates by Ananain and Bromelain

Ananain used for this example was obtained by the method described in Example 1: the bromelain used was as in Example 4.

For the determination of kinetic parameters $K_m$ (the Michaelis Constant) and $k_{cat}$ (the turnover number) of hydrolysis of Z-Phe-Arg-NHMec and Z-Arg-Arg-NHMec, measurements of the initial rates of reaction were made in 0.007% Brij 35 at 40° C. The enzymes ($1 \times 10^{-11}$M to $1 \times 10^{-9}$M final concentration of activatable enzyme as determined by active-site titration) were activated in 0.75 ml of 4-fold concentrated buffer in a fluorimetric cuvette at 40° C. for 2 min, to which pre-warmed 0.01% Brij was added, followed by substrate to a final volume of 3.0 ml. Continuous rate assays were carried out using a temperature-controlled cell, with stirring, in the fluorimeter (360 nm emission, 460 nm excitation), standardized so that 1000 arbitrary units corresponded to 0.2 μM coumarin (i.e. at most, 10% substrate hydrolysis). Substrate concentration(s) used were in the range 2 to 100 μM. Visual inspection of the data was performed using the direct linear plot and plots of s/v against s (v being the rate of product formation). (Henderson, P. J. F., Techniques in Protein and Enzyme Biochemistry, B113, 1-43, 1978). Values of $K_m$ and $V_{max}$ (the maximum rate of product formation at a given enzyme concentration) were calculated by the method of Wilkinson, G. N., Biochem. J., 80, 324-332, 1961.

The kinetic parameters $K_m$ and $k_{cat}$ are shown in Table 3.

TABLE 3

Kinetic parameters of hydrolysis of two fluorozenic substrates by ananain and bromelain

| Proteinases | Substrates | $K_m$ ($\mu M$) | $k_{cat}$ ($s^{-1}$) | $k_{cat}/K_m$ ($s^{-1} \cdot \mu M^{-1}$) |
|---|---|---|---|---|
| Ananain | Z-Phe-Arg-NHMec | 48.3 ($\pm$4.8) | 7.07 ($\pm$0.3) | 0.146 ($\pm$0.02) |
| | Z-Arg-Arg-NHMec | 44.5 ($\pm$9.0) | 0.323 ($\pm$0.03) | 0.007 ($\pm$0.002) |
| Bromelain | Z-Phe-Arg-NHMec | 83.1 ($\pm$14.1) | 0.14 ($\pm$0.01) | 0.0016 ($\pm$0.0003) |
| | Z-Arg-Arg-NHMec | 15.4 ($\pm$2.8) | 27.3 ($\pm$1.9) | 1.77 ($\pm$0.37) |

(The numbers in parentheses are standard deviations from the mean.)

EXAMPLE 6

SDS Gel Electrophoresis

The discontinuous 2-amino-2-methylpropane-1,3-diol (Ammediol)/glycine/HCl system was employed in slab gels containing 12.5% total acrylamide as described by Bury, A., J. Chromatog, 213, 491-500, 1981. To calibrate each gel for relative molecular mass, there was run a mixture of standard proteins: phosphorylase a, 100,000; transferrin, 78,000; bovine serum albumin, 68,000; IgG heavy chain, 50,000; carbonic anhydrase, 29,000; IgG light chain, 25,000; soya bean trypsin inhibitor, 21,000; cytochrome c, 12,750. Gels were stained with 1% Brilliant Blue G in methanol/acetic acid/water (50:20:30, v/v/v) before storing in 1% formic acid.

Figure 4:
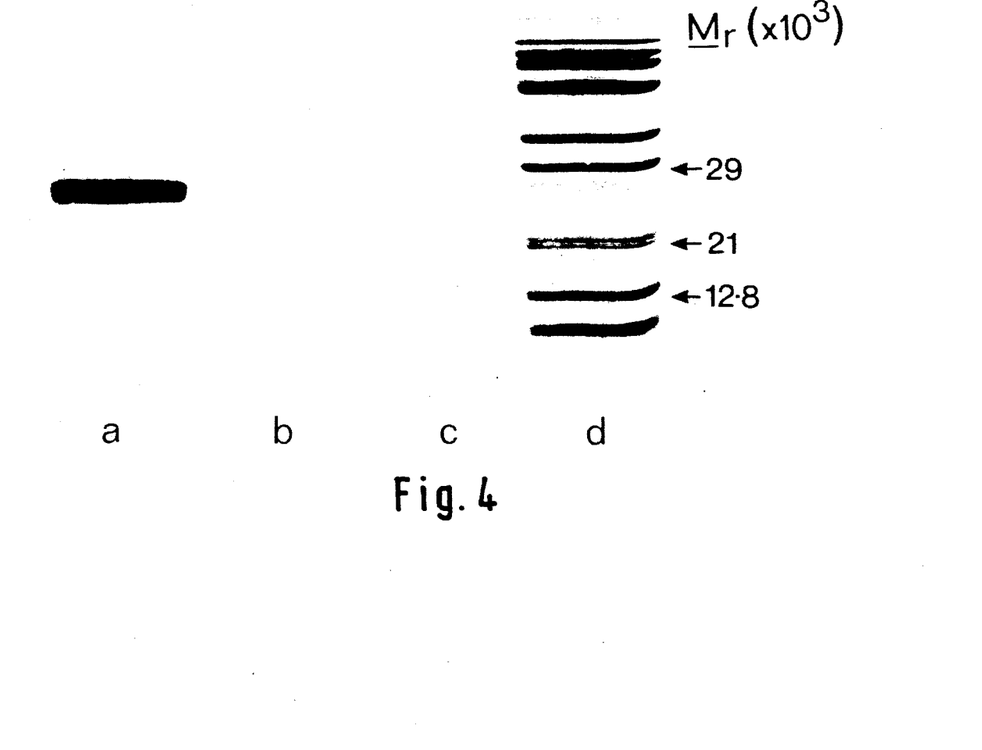
FIG. 4 depicts SDS gel electrophoresis of bromelain and ananain.

To an aliquot containing 5 $\mu g$ of a given pineapple extract was added an equal volume of 25% (w/v) trichloro-acetic acid. This was mixed and centrifuged. The supernatants were removed and the pellets washed twice in acetone and then left to dry for 30 min at room temperature. Each was then resuspended in 50 $\mu l$ of sodium dodecyl sulphate (SDS) sample buffer containing mercaptoethanol, boiled for 3 min and then run on a 12.5% polyacrylamide SDS gel. (See accompanying FIG. 4: Lane a—Sigma "Bromelain"; Lane b—affinity purified bromelain; Lane c—affinity purified ananain; Lane d—molecular weight markers.)

EXAMPLE 7

Multizonal Cathodal Electrophoresis

Figure 5:
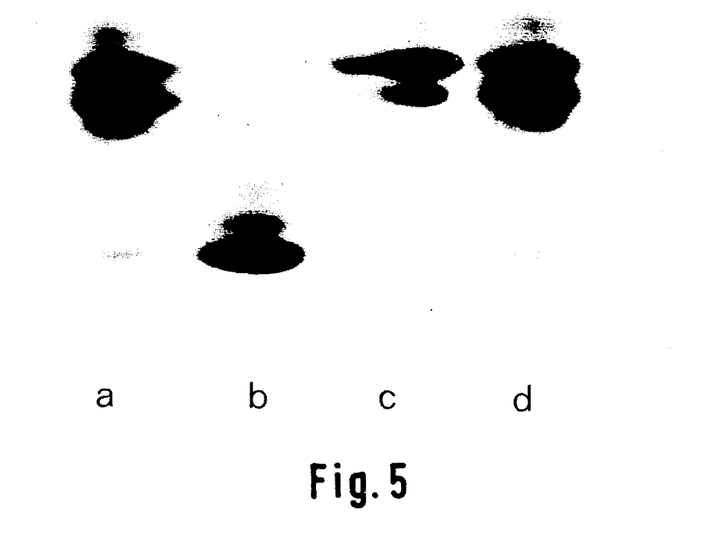
FIG. 5 depicts multizonal cathodal gel electrophoresis of bromelain and ananain.

The method of Zucker S., et al, Biochimica et Biophysica Acta, 828, 196-204, 1985 was used to separate the native constituents of Sigma "Bromelain" by electrophoresis. (See accompanying FIG. 5: Lanes a and d—Sigma "Bromelain" (10 $\mu g$); Lane b—affinity purified ananain (10 $\mu g$); Lane c—affinity purified bromelain (10 $\mu g$).)

EXAMPLE 8

Titration of Enzymes

Each of the three major purified proteinases from pineapple stem were titrated with the irreversible cysteine proteinase inhibitor, E-64 (Barrett A. J., et al., Biochem. J., 201, 189-198, 1982).

The amount of enzyme protein was determined using an $\xi_{1\%, 280} = 52,500$ (assuming a relative molecular mass of 25,000 for the three enzymes and using the published $A_{1\%, 280}$ of 20.1 cited in Example 1). For bromelain, 0.8 $\mu M$ of the enzyme protein (final concentration) was added to 11 tubes. 250 $\mu l$ of 4-fold concentrated buffer (0.4M sodium phosphate, 4 mM EDTA, 8 mM DTT, pH 6.8) was added to these tubes, followed by 0.08 $\mu M$ increments from 0 to 0.8 $\mu M$ (final concentration) of E-64. Tubes were left for 15 minutes at 40° C., after which pre-warmed 0.01% Brij 35 was added to 750 $\mu l$. 250 $\mu l$ of 6% azocasein was then added and the mixture incubated for 1 hour at 40° C. The reaction was stopped by addition of 5.0 ml of 3% (w/v) trichloroacetic acid, and the $A_{366}$ of the filtrates was determined.

Figure 6:
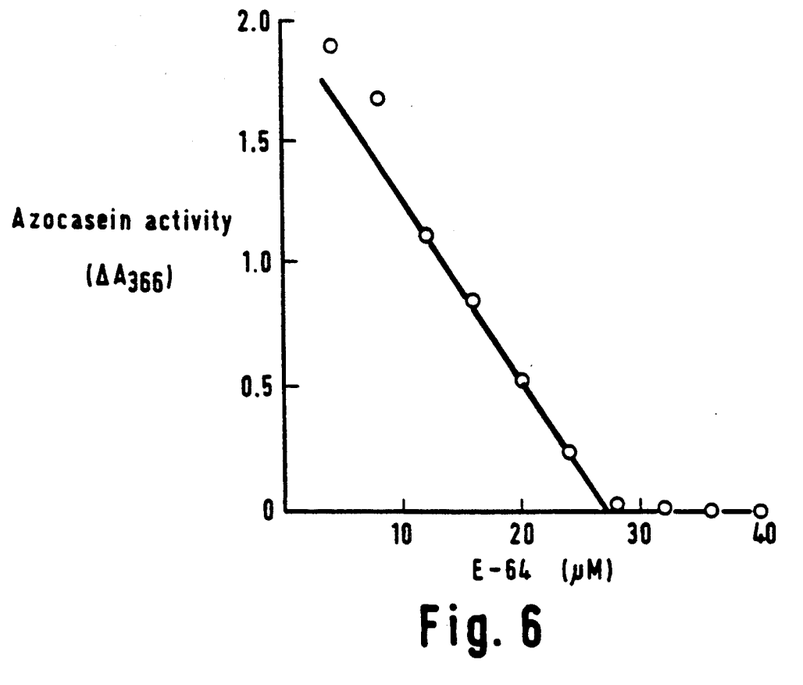
FIG. 6 depicts titration with proteinase inhibitor, E-64, for ananain.

For ananain and comosain, 2 $\mu M$ enzyme final concentration was used, with 0.2 $\mu M$ increments from 0 to 2 $\mu M$ E-64. Plots of $A_{366}$ against E-64 concentration were made, the x-axis intercept being the concentration of active enzyme. (See accompanying FIG. 6.)

EXAMPLE 9

Immunological Studies

A non-specific antiserum to crude Sigma pineapple stem extract was raised in a rabbit using intramuscular injections of 1.0 mg of filtered material in phosphate buffered saline (PBS) and Freund's adjuvant, at monthly intervals. Periodic bleeds were taken which were allowed to clot at 37° C. for 1 hour and left overnight at 4° C. for the clot to retract. The released serum was then pipetted off and stored at −20° C. The final bleed was obtained by cardiac puncture and the serum was obtained in the same fashion.

An antiserum was also obtained using ananain (obtained by the method described in Example 1) as antigen by this method.

Double immunodiffusion plates were run using these antisera against bromelain peak 1 from accompanying FIG. 1 and ananain obtained by the method described in Example 1.

Figure 7:
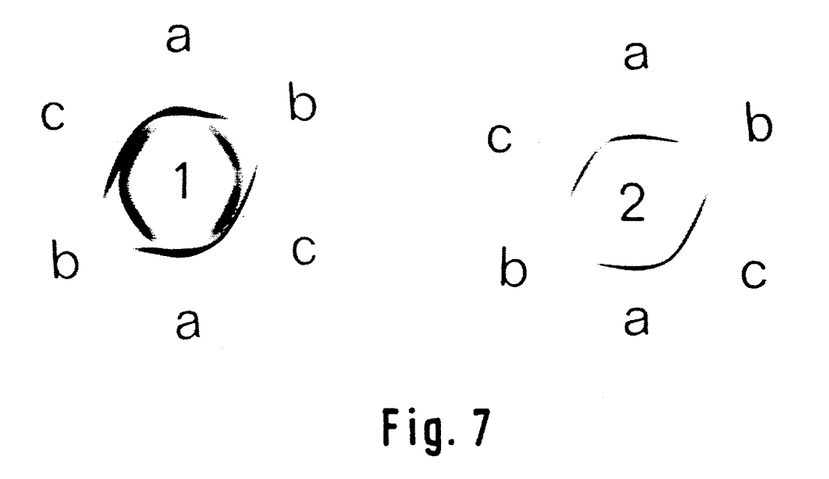
FIG. 7 depicts double immunodiffusion of bromelain and ananain.

Plates were poured with 1% agarose in PBS, pH 7.2. Holes were cut using a template and 20 $\mu l$ of the relevant antiserum was added to the central well. Plates were left to develop for 24 hours at room temperature before being washed for 48 hours in 1% NaCl. The plates were then dried and stained with 1 mg/ml Coomassie Brilliant Blue G (Sigma) in 2% sodium formate, 3.5% formic acid, 33% ethanol for 30 minutes. Destaining was with the above buffer minus the dye for about 5 minutes. (See accompanying FIG. 7: Well a—ananain; Well b—bromelain peak 1; Well c—ananain and bromelain mixed; Well 1—anti-(pineapple extract) serum; Well 2—anti-(ananain) serum.)

EXAMPLE 10

Kinetics of Inhibition of Ananain and Bromelain by Chicken Cystatin

The chicken cystatin was a mixture of forms 1 and 2 purified by affinity chromatography (Anastasi, A., et al., Biochem. J., 211, 129-138, 1983). The concentration of active cystatin was determined by titration with papain which had previously been standardised by E-64 titration (Zucker et al., loc cit).

For the determination of the $K_{i(app)}$ (apparent dissociation constant in the presence of substrate) for the reaction between chicken cystatin and ananain, continuous rate experiments were performed in a fluorescence spectrometer in a thermostatted fluorimetric cuvette at 40° C. The enzyme ($2 \times 10^{-10}$M final concentration of activatable ananain) was activated in 0.75 ml of 0.40M sodium phosphate buffer, pH 6.8, containing 4 mM EDTA, 8 mM dithiothreitol and 0.02% Brij 35, for 2 min. Pre-warmed water was then added, followed by the substrate Z-Phe-Arg-NHMec (5 μM final concentration), to a final volume of 3 ml. The rate of the reaction in the absence of inhibitor ($v_o$) was recorded, after which inhibitor (ranging from $5 \times 10^{-10}$ to $4 \times 10^{-9}$M final concentration of active chicken cystatin) was added in a negligible volume, with mixing. The initial rate was allowed to relax to the new steady state in the presence of inhibitor ($v_i$). The data was replotted as ($v_o/v_i$) $-1$ against I (inhibitor concentration), yielding a straight line, passing through the origin, of slope $1/K_{i(app)}$ (Nicklin, M. J. H., and Barrett, A. J., Biochem. J., 233, 245-253, 1984).

For the determination of the $K_{i(app)}$ for the reaction between chicken cystatin and bromelain, the reaction conditions were as described above, with the following exceptions. The concentration of activatable bromelain was $5 \times 10^{-11}$M, the range of active chicken cystatin concentrations used was $1 \times 10^{-7}$ to $5 \times 10^{-7}$M, and the substrate used at 5 μM final concentration was Z-Arg-Arg-NHMec.

The $K_{i(app)}$ for the inhibition of ananain by chicken cystatin was found to be $1.2 \times 10^{-9}$M. The $K_{i(app)}$ for the reaction of bromelain with chicken cystatin was found to be $4.8 \times 10^{-5}$M.

EXAMPLE 11

Debridement of Burn Wounds in a Rat Model

Young male albino rats (Charles River) were anaesthetized, shaved on their backs and subjected to a 100° C. scald burn for 15 seconds. After a 24 hour recovery period, each rat was again anaesthetized and four silicone rubber dams were attached by dermal glue to sites on the burn wound. Phosphate-buffered saline was applied to saturate gauze pads placed within the confines of the dams. The sites were maintained in a moist state by wrapping a plastic film around the body of each animal. After 1 hour, the wraps and gauze pads were removed and fresh gauze was placed within the dams. Partially purified ananain and comosain were titrated with E-64 (see Example 8). Solutions (1 ml) containing dithiothreitol-activated ananain (4 mg active enzyme), comosain (4 mg active enzyme) or a control solution of phosphate-buffered saline containing dithiothreitol were added to saturate the gauze pads. At 1 hour, the sites were exposed, gently scraped with a blunt scalpel to remove digested eschar and evaluated for the extent of debridement. An additional 0.5 ml (containing 2 mg of active enzyme or phosphate-buffered saline containing dithiothreitol) was then added to each gauze pad and debridement continued for an additional hour. At this time (2 hours), the site was again exposed, scraped and evaluated. An additional 0.5 ml of solution was again added and debridement continued. After another hour, the site was scraped and a final evaluation conducted. Debridement was scored by visual inspection according to the following criteria:

0—No visible change.
1—Partial, but not full thickness debridement.
2—Debridement to expose underlying pink tissue.
3—Debridement to expose pink to red underlying tissue with petechiae.
4—Debridement of visible eschar accompanied by bleeding.

Figure 8A:
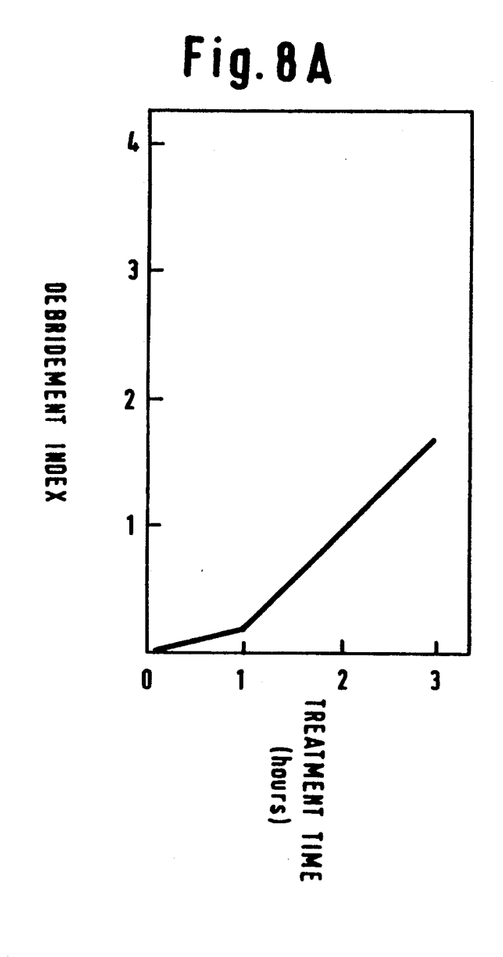
FIGS. 8A, 8B and 8C depict debridement of rat burn wound with saline, comosain and ananain, respectively.
Figure 8B:
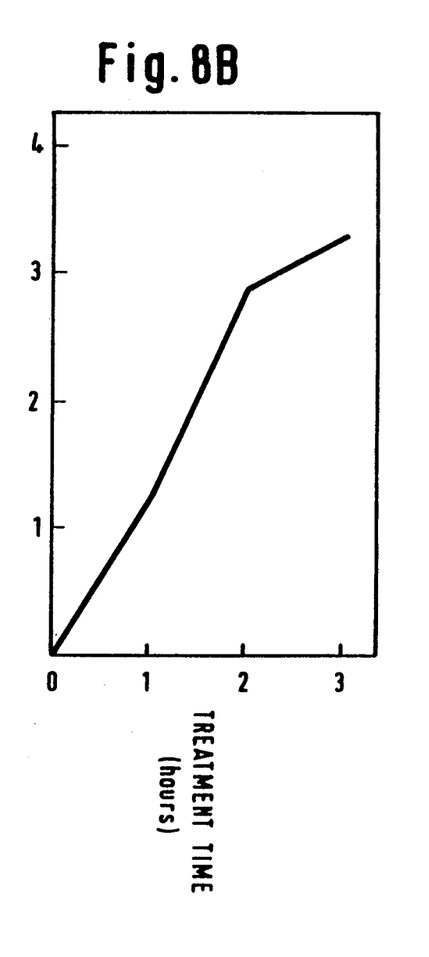
Figure 8C:
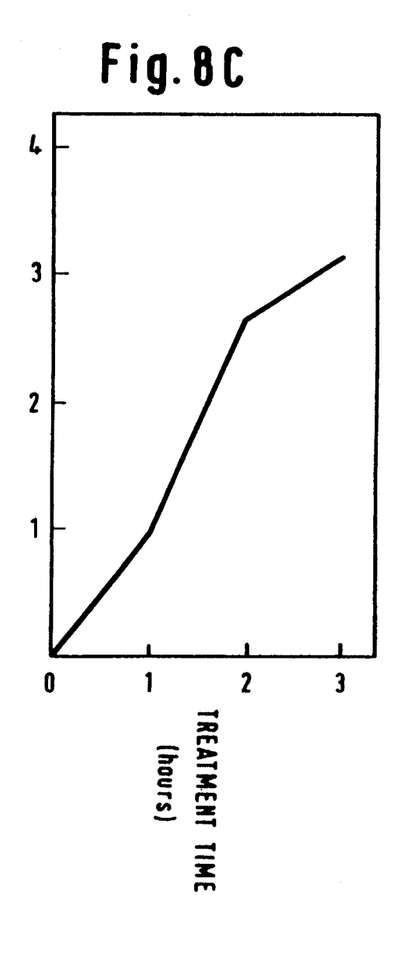

Both enzyme solutions were effective in debriding the burn wounds as illustrated graphically in accompanying FIG. 8.

TABLE 4

Debridement of rat burn wound

| Experimental Group | Treatment Time (hours) | Debridement Index (mean ± S.Dev., n = 12) |
|---|---|---|
| A Control (Phosphate-buffered saline) | 1 | 0.375 ± 0.73 |
|  | 2 | 1.068 ± 0.495 |
|  | 3 | 1.805 ± 0.666 |
| B Comosain | 1 | 1.208 ± 0.819 |
|  | 2 | 2.943 ± 0.416 |
|  | 3 | 3.388 ± 0.474 |
| C Ananain | 1 | 1.069 ± 0.756 |
|  | 2 | 2.694 ± 0.553 |
|  | 3 | 3.153 ± 0.463 |

What is claimed is:

1. A purified cysteine proteinase derived from pineapple plant material having a molecular weight of about 25,000 daltons and exhibits activity toward the coumarylamide substrate Z-Gly-Phe-Cit-NHMec, said activity being determined at a substrate concentration of 5 uM, said cysteine proteinase exhibiting preferential activity toward the coumarylamide substrate Bz-Phe-Val-Arg-NHMec.

2. A purified cysteine proteinase derived from pineapple plant material having a molecular weight of about 25,000 daltons and exhibits activity toward the coumarylamide substrate Z-Gly-Phe-Cit-NHMec, said activity being determined at a substrate concentration of 5 uM, said cysteine proteinase exhibiting preferential activity toward the coumarylamide substrate Z-Arg-Arg-NHMec.

3. A mixture of two cysteine proteinases derived from pineapple plant material characterized in that each proteinase in said mixture has a molecular weight of about 25,000 daltons and exhibits activity toward the coumarylamide substrate Z-Gly-Phe-Cit-NHMec, said activity being determined at a substrate concentration of 5 uM, one of said proteinases exhibiting preferential activity toward the coumarylamide substrate Bz-Phe-Val-Arg-NHMec, and the other proteinase exhibiting preferential activity toward the coumarylamide substrate Z-Arg-Arg-NHMec.

4. A process for the isolation of a cysteine proteinase from pineapple plant material as claimed in any of claims 1 or 2 comprising the use of at least one technique selected from the group consisting of cation exchange chromatography, affinity chromatography and high resolution cation exchange chromatography wherein the cysteine proteinase is separated and purified from said pineapple plant material.

5. A process as claimed in claim 4 wherein the plant material is powdered stem.

6. A topical pharmaceutical composition comprising a cysteine proteinase as claimed in any of claims 1, 2, or 3 and a pharmaceutically acceptable carrier.

7. A method for the debridement of eschar tissues comprising applying thereto a therapeutically effective amount of a pharmaceutical composition as claimed in claim 6.

8. The pharmaceutical composition of claim 6 which additionally contains a thickening agent and is in the form of a gel or ointment.

* * * * *